United States Patent
Wieslander et al.

[19]

[11] Patent Number: 6,039,719
[45] Date of Patent: Mar. 21, 2000

[54] BAG FOR CONTAINING A STERILE MEDICAL SOLUTION AND METHOD OF MIXING A STERILE MEDICAL SOLUTION

[75] Inventors: Anders Wieslander, Lund, Sweden; Giorgio Cappelli, Genoa, Italy

[73] Assignee: Gambro AB, Sweden

[21] Appl. No.: 09/011,411

[22] PCT Filed: Aug. 6, 1996

[86] PCT No.: PCT/SE96/00989

§ 371 Date: Feb. 6, 1998

§ 102(e) Date: Feb. 6, 1998

[87] PCT Pub. No.: WO97/05852

PCT Pub. Date: Feb. 20, 1997

[30] Foreign Application Priority Data

Aug. 8, 1995 [SE] Sweden ................................ 9502769

[51] Int. Cl.[7] ................................................ A61B 19/00
[52] U.S. Cl. ........................ 604/410; 604/416; 206/219
[58] Field of Search .................... 604/87, 408, 410, 604/415, 416; 206/219, 222, 221; 383/38, 41

[56] References Cited

U.S. PATENT DOCUMENTS

| | | |
|---|---|---|
| 3,187,750 | 6/1965 | Tenczar, Jr. . |
| 3,520,471 | 7/1970 | Faust . |
| 3,545,671 | 12/1970 | Ross ........................ 604/410 |
| 3,985,135 | 10/1976 | Carpenter et al. ....................... 604/410 |
| 4,396,383 | 8/1983 | Hart ........................................... 604/82 |
| 4,403,992 | 9/1983 | Bertellini et al. . |
| 4,484,920 | 11/1984 | Kaufman et al. ........................ 604/416 |
| 4,496,046 | 1/1985 | Stone et al. . |
| 4,507,114 | 3/1985 | Bohman et al. ......................... 604/411 |
| 4,997,083 | 3/1991 | Loretti et al. . |
| 5,114,004 | 5/1992 | Isono et al. .............................. 206/222 |
| 5,209,347 | 5/1993 | Fabisiewicz et al. .................... 206/219 |
| 5,431,496 | 7/1995 | Balteau et al. ............................. 383/38 |
| 5,560,403 | 10/1996 | Balteau et al. ........................... 206/219 |

FOREIGN PATENT DOCUMENTS

| | | |
|---|---|---|
| 0 442 406 A1 | 8/1991 | European Pat. Off. . |
| 0 619 998 A1 | 10/1994 | European Pat. Off. . |
| 38 30 630 A1 | 3/1990 | Germany . |
| 41 07 223 C1 | 9/1992 | Germany . |
| 93/09820 | 5/1993 | WIPO . |

*Primary Examiner*—Corrine McDermott
*Assistant Examiner*—David J. Cho
*Attorney, Agent, or Firm*—Lerner, David, Littenburg, Krumholz & Mentlik, LLP

[57] ABSTRACT

A container for enclosing a sterile medical solution and method for mixing the same, such as a peritoneal dialysis solution. The container comprises a first compartment comprising the major part of the solution, such as an electrolyte solution comprising NaCl, $CaCl_2$, etc., and two separate compartments, each comprising glucose in a high concentration. The entire container is autoclaved including the solutions as separated, thereby minimizing the formation of toxic products. During preparation for use, the second compartment or the third compartment, or both, are connected to the first compartment by breaking pins in a connection tube for each compartment. Depending upon the compartments connected to the first compartment, a different concentration of glucose results. Thus, all three of the usually employed glucose concentrations may be provided in a single container.

12 Claims, 12 Drawing Sheets

BAG FOR CONTAINING A STERILE MEDICAL SOLUTION AND METHOD OF MIXING A STERILE MEDICAL SOLUTION

FIELD OF THE INVENTION

The present invention relates to a bag for containing a sterile medical solution, comprising glucose or glucose-like compounds, for example a solution for peritoneal dialysis, or a nutritional solution.

BACKGROUND OF THE INVENTION

The present invention starts from what is disclosed in WO 93/09820, relating to a system where the glucose or glucose-like compounds are included in a first package at a high concentration whilst the remaining compounds are separately packed in a second package. The packages are preferably combined into a single, two compartment bag. The packages, or bag, are heat sterilized, preferably autoclaved in a conventional way. The high glucose concentration in the first package protects the glucose or glucose-like compounds from deterioration, which otherwise results in the formation of toxic compounds. Other factors influencing upon the formation of toxic compounds from the glucose or glucose-like compounds are low pH, absence of electrolytes, absence of oxygen contents, short exposure times (at higher temperature) etc.

Bags comprising several compartments are shown in, for example, U.S. Pat. No. 4,403,992 disclosing a bag device for continuous peritoneal dialysis having two chambers one being a dialysis liquid chamber and one being a disinfectant chamber. First the disinfectant is passed through the respective ducts, whereupon the dialysis liquid is passed through the same duct.

Another bag having several chambers is disclosed DEC1-41 07 223. This bag has a specific frangible web between the chambers being openable for mixing the contents of the two chambers.

Another double compartment container is disclosed in EP-A1-619 998. This container includes a peelable seal constructed from a multilayer film.

A multicompartment flexible bag is disclosed in DE-A1-38 30 630 comprising a clamp dividing the bag into two compartments. By removing the clamp, the contents of the compartments can be mixed.

U.S. Pat. No. 3,520,471 discloses a sealed flexible container for carrying fluids particularly collecting, storing and dispensing blood. The container has an inclined end seal for improving the possibility to empty the container.

U.S. Pat. No. 4,496,046 discloses a multiple chamber container for the medical field such as nutrition solutions. The bag is composed of two or three compartments for mixing different solutions.

SUMMARY OF THE INVENTION

The object of the present invention is to improve the bag shown in WO 93/09820 to make it more convenient to use, to make the mixing of the two liquids more efficient and to adapt the bag to easy and convenient construction and use by the end consumer and improve the logistic handling and storing of the bag.

These objects are met by a bag as defined in the appended patent claims.

BRIEF DESCRIPTION OF THE DRAWINGS

Further objects, features and advantages of the present invention will appear from the following detailed description of preferred embodiments of the invention shown on the enclosed drawings.

DETAILED DESCRIPTION

Figure 1:
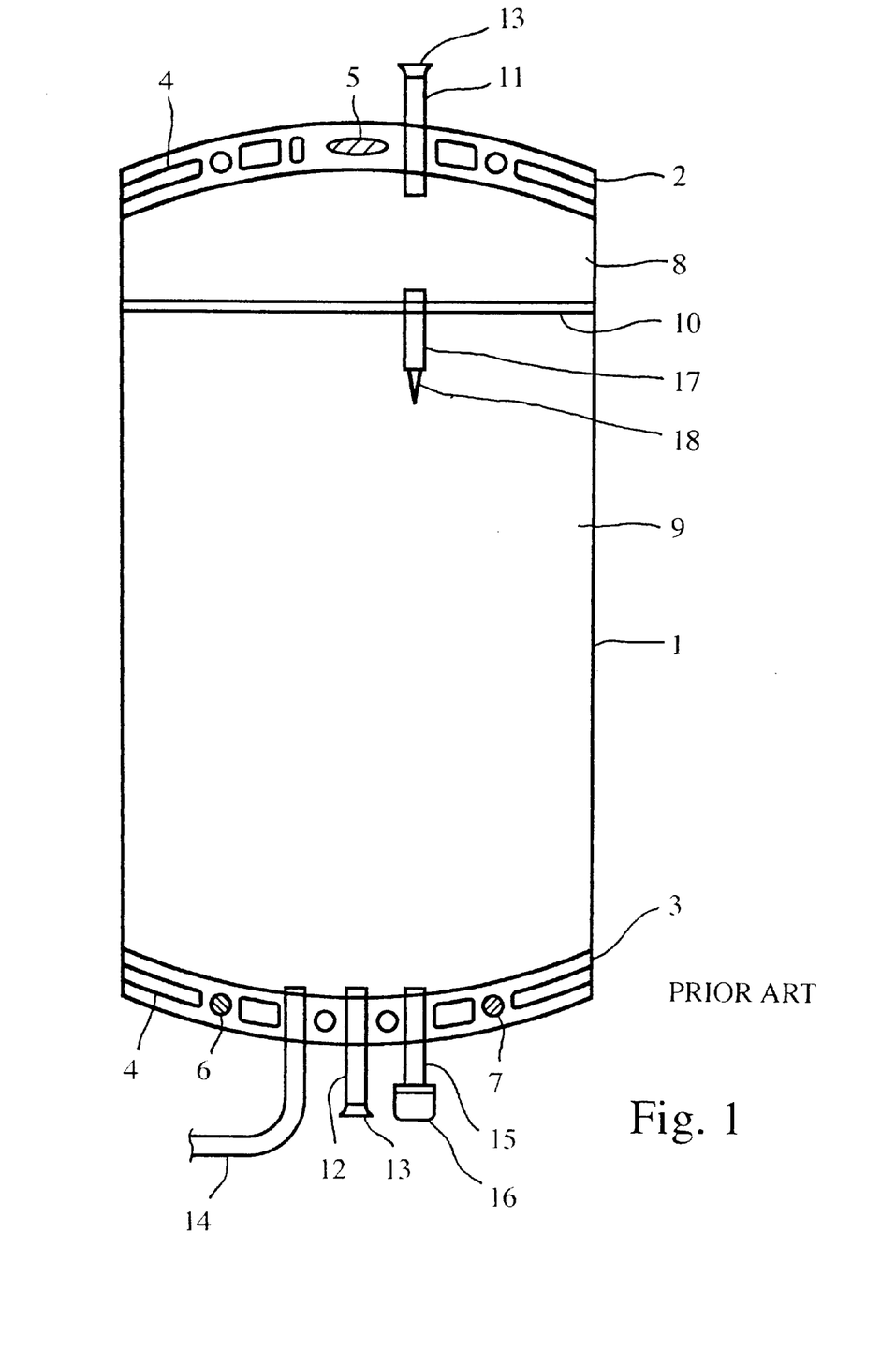
FIG. 1 is a plan view of a bag according to WO 93/09820 showing the prior art.

FIG. 1 is a plan view of a flexible bag according to WO93/09820. The bag is intended to include a solution for peritoneal dialysis and has a size of approximately two and a half liters.

The bag is made from a continuous tube of a plastics material, which is sealed at both ends by sealing borders 2,3.

As shown in FIG. 1 each sealing border comprises several embossments 4 and apertures 5,6,7. The embossments 4 enhance the stability of the border 2. The aperture 5 in the upper border 2 is intended for hanging the bag during use and the apertures 6,7 in the lower border 3 are for fixation of the bag during the manufacturing operation.

The bag is divided into two compartments 8,9 by separation means such as a welding seal line 10. The small upper compartment 8 comprises a concentrated glucose solution having a concentration of about 50%. The large lower compartment 9 comprises all other electrolytes necessary for the solution to be formed, such as NaCl, $MgCl_2$, $CaCl_2$, lactate etc, dissolved in water in a manner known per se. If the bag should be used as a nutritional solution, the large compartment may comprise only NaCl or any suitable composition as used today but excluding glucose. The entire bag filled with solution is sterilized, preferably by autoclaving at 120° C. during 20 minutes.

It is mentioned that the glucose can be exchanged with a glucose-like compound, such as glucose polymers, as an osmotic agent.

In order to obtain access to compartments 8 and 9 during the manufacturing process, the borders 2,3 are perforated by introduction tubes 11,12. Such tubes 11,12 are inserted in borders 2,3 during the welding procedure. Initially, tubes 11,12 are long enough and/or provided with connection means to be automatically connected to a filling equipment of the manufacturing plant. After filling compartments 8,9, the tubes are cut and sealed by heat as shown by end portions 13 in FIG. 1.

The lower border 3 is also provided with an outlet tube 14, which connects compartment 9 with the consumer, for example a catheter ending in the abdominal cavity of a patient for peritoneal dialysis. Often tube 14 terminates in a luer connector (not shown in FIG. 1).

Furthermore, border 3 is provided with a medicament tube 15 including a removable cap 16. When cap 16 is removed, tube 15 forms an entrance site for introducing any type of beneficial agent or medicament into compartment 9 as desired, such as antibiotica.

Welding line 10 is provided with a connection tube 17 initially closed by a breakable portion 18. When portion 18 is broken, communication is established between compartment 8 and compartment 9. While compartment 8 comprises glucose of high concentration having a high density, the glucose will flow down through tube 17 into the lower compartment 9 and mix with the contents thereof. After a few minutes, compartment 8 is completely empty. Any residual fluid can be forced out from compartment 8 manually.

As appears from FIG. 1, tube 17 is placed in line with introduction tube 11. The reason for this is that it is more easy to insert tubes 11 and 17 if they are in line during the manufacturing step. Both tubes are attached to a mandrel interposed in the bag blank before welding, whereupon the welding step is performed. After welding, the mandrel is withdrawn. Preferably, the welding takes place by high frequency welding but of course any other type of heat welding or sealing (glueing) would be suitable depending on the material.

Figure 2:
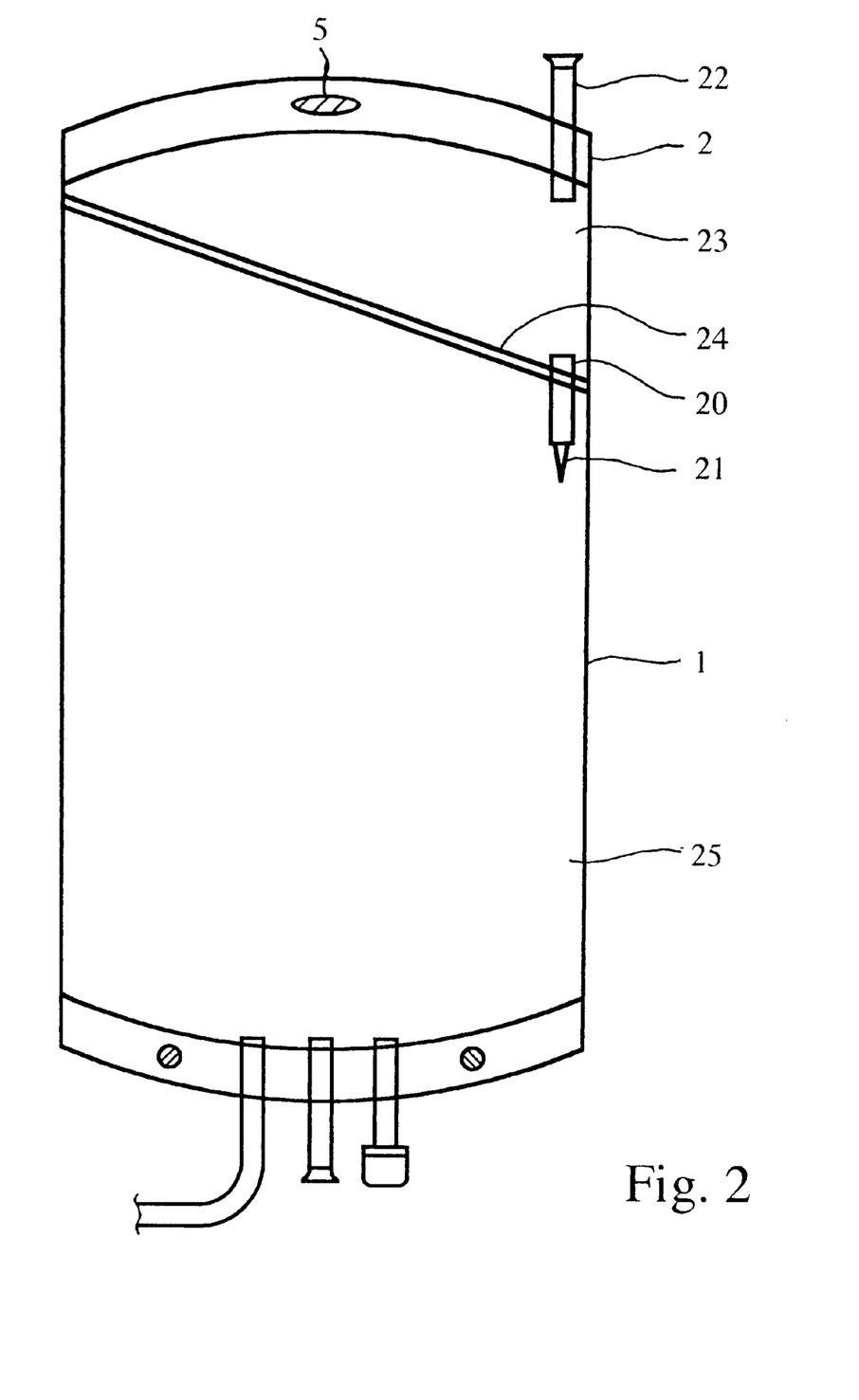
FIG. 2 is a plan view of a first embodiment of the bag according to the present invention.

FIG. 2 shows a first embodiment of the present invention. It has been found difficult for the user to break the breakable portion 18 of tube 17 when it is placed too close to the middle. It is desired to have tube 17 closer to the side edge of the bag 1. This side-way placement of the connection tube 20 including a breakable portion 21 is clearly shown in FIG. 2. In this position, the breakable portion 21 is easily accessible since it is positioned very close to the side of bag 1. Preferably, the introduction tube 22 is placed in line with tube 20 as shown.

In order to improve the emptying of upper compartment 23, the welding line 24 between compartment 23 and compartment 25 is inclined and slopes towards connection tube 20. Since the glucose solution contained in compartment 23 has a higher density than water including electrolytes comprised in compartment 25 the glucose solution will flow along welding line 24 towards the connection tube 20 and enter the lower compartment 25 to mix with the contents thereof.

The glucose solution in compartment 23 has a rather high viscosity and sometimes the mixing time will be experienced to be long. One obvious way of decreasing the mixing time is to include a connection tube 20 having a larger area. In some cases, however, such a higher diameter tube 20 is difficult to include within the welding line 24 without the risk of 25 leakages.

Figure 3:
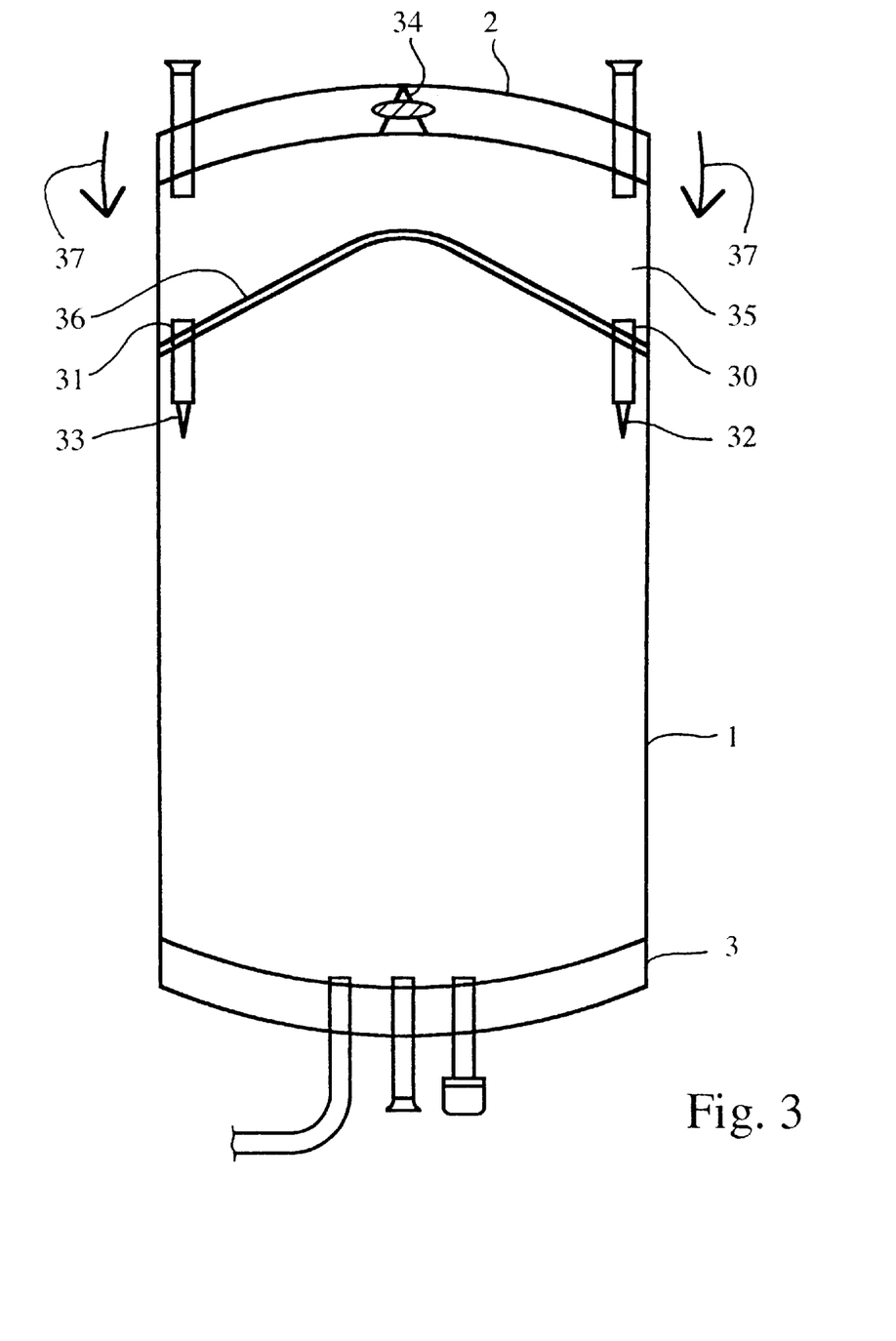
FIG. 3 is a plan review of eight further embodiment of the bag according to the invention.

Thus, according to FIG. 3, it is suggested to use two connection tubes 30,31 adjacent each side edge of bag 1. By breaking both breakable portions 32,33, a more rapid mixing of the two liquid components is obtained. Moreover, the complete mixing of the two liquids with each other is improved by entering the liquid in two places. While this might not be so important for a liqiud for peritoneal dialysis, it is more important for nutritional solutions.

Moreover, the upper border 2 is provided with weakening lines 34. When the breakable portions 32,33 are broken and compartment 35 starts to empty itself, the left and right side of border 2 will move downwards according to arrows 37 to form an inverted V-shape. This movement is facilitated by the weakening lines 34 and the shape of the welding line 36 and the fact that border 2 is rather rigid. Such movements along arrows 37 will excert a pressure against the contents of compartment 35 which decreases the time necessary for the emptying of compartment 35. The border portions 2 will tend to squeeze out the contents of compartment 35.

A dialysis solution for peritoneal dialysis is usually provided in three different concentrations, viz. 1,5%, 2,5%, 4% of glucose concentration in the final solution. By using a three compartment bag, previously known per se, all three concentration levels can be obtained in a single bag. In this third embodiment, shown in FIG. 4, of the present invention, the upper compartment is divided into two compartments of equal size by a welding line 41 and two sloping welding lines 42,43. Thus, there is formed a first upper compartment 44 and a second upper compartment 45, each being accessed via introduction tubes 46,47. The first compartment 44 comprises glucose solution having a concentration of about 30% and the second compartment 45 comprises a glucose solution having a concentration of about 50%.

Figure 4:
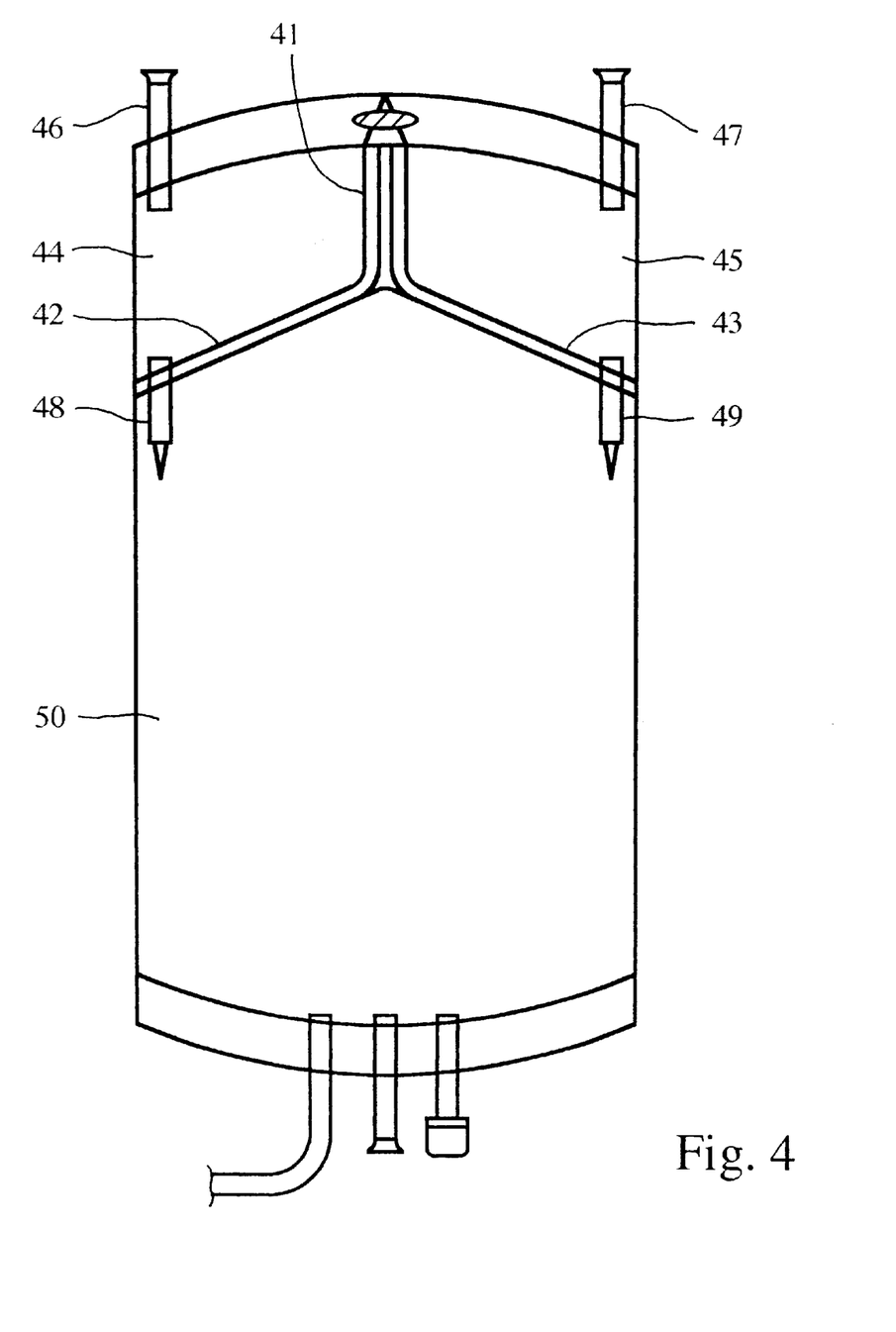
FIG. 4 is a plan view of another embodiment of the bag according to the invention.

When breaking the breakable portion of connection tube 48, the contents of the first compartment 44 is mixed with the contents of the lower compartment 50 to form a peritoneal dialysis solution having a concentration of 1,5% of glucose. If the breakable portion of connection tube 49 is broken, the contents of compartment 45 is mixed with the contents of both compartment 50 thereby forming a dialysis solution having a concentration of about 2,5% of glucose. If both breakable portions of connection tubes 48,49 are broken, the contents of both compartments 44 and 45 are mixed with the contents of compartment 50 thereby to form a dialysis solution having a concentration of about 4% of glucose.

In this way it is only necessary to store one type of bag for all three concentrations. While one and the same patient may use solutions of different concentrations during different times of the day or different days, the operation for the patient will also be improved. Other combinations of concentration levels can easily be achieved. Further different concentration can be obtained by including further compartments, such as four or five compartments.

It is noted that some glucose is wasted when the bag is used for the two lower concentrations, since one of the two glucose compartments is left unused. However, glucose is an inexpensive material. Moreover, glucose can easily be discarded, since it does not harm the environment to any large extent. The advantages of providing one bag for all three concentrations in economical terms and handling terms far outweigh this drawback.

Figure 5:
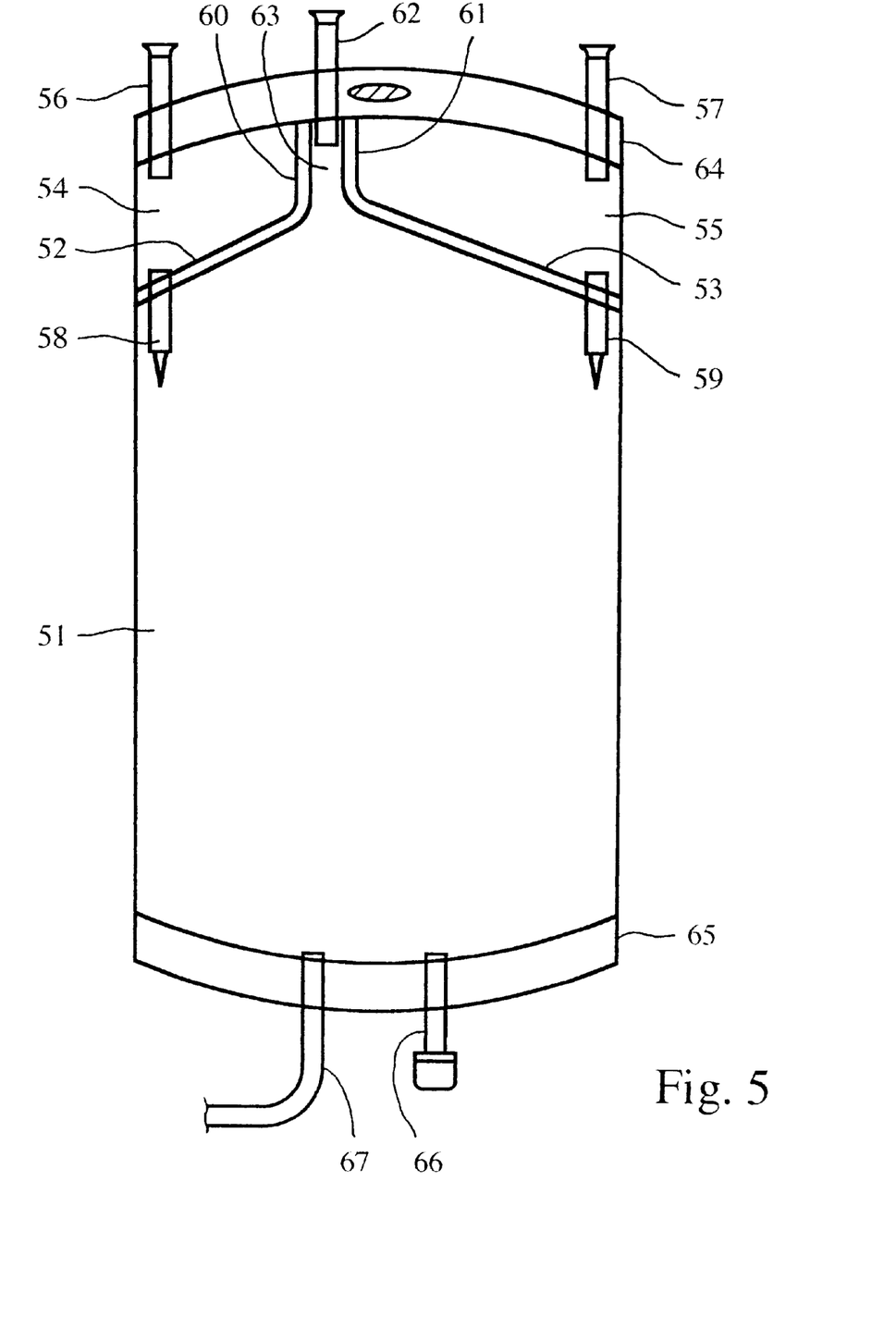
FIG. 5 is a plan view of a further embodiment of the bag according to the invention.

FIG. 5 shows another embodiment of the invention which very much ressembles the embodiment shown in FIG. 4. The first compartment 54 and the second compartment 55 (corresponding to compartments 44 and 45) have different sizes but accomodated glucose solution of the same concentration, for example 50%. Thus, the same possibilities appears as from the third embodiment shown in FIG. 4.

One example of a PD solution according to the embodiment of FIG. 5 is given below. The first upper compartment 54 comprises 60 ml glucose at 50% and the second upper compartment 55 comprises 100 ml glucose of 50%, both at a pH of 3—3,5.

The lower compartment 51 comprises 1900 ml of electrolytes having a pH of about 6,5. The electrolytes are: 264 mMoles Na$^+$, 190 mMoles Cl$^-$, 2,7 mMoles Ca$^{++}$, 0,5 mMoles Mg$^{++}$ and 80 mMoles lactate. After mixing, the lower compartment 51 includes a solution having 1,53%, 2,5% or 3,88% glucose concentration and the following electrolytes concentrations: Na$^+$ 128–135 mM, Cl$^-$ 92–97 mM, Ca$^{++}$ 1,31–1,38 mM, Mg$^{++}$ 0,24–0,26 mM and lactate 38–41 mM, depending on which compartments have been mixed.

Moreover, the embodiment according to FIG. 5 is provided with a channel 63 positioned between welding lines 60 and 52 forming the first compartment 54 and welding lines 61 and 53 forming the second compartment 55 as clearly shown in FIG. 5. The upper border 64 of the bag is provided with two introduction tubes 56 and 57, for introduction of the glucose solution. Moreover, border 64 is provided with a third introduction tube 62 ending in channel 63 for providing the electrolyte solution into compartment 51. The second lower border 65 is only provided with a tube 66 for introduction of a medicament and a tube 67 for connection to the patient but lacks an introduction tube shown in the previous embodiments.

By having all three introduction tubes 56,57,62 in the upper border 64, several manufacturing advantages are obtained since all filling equipment now can be placed on one side of the manufacturing line.

Figure 6:
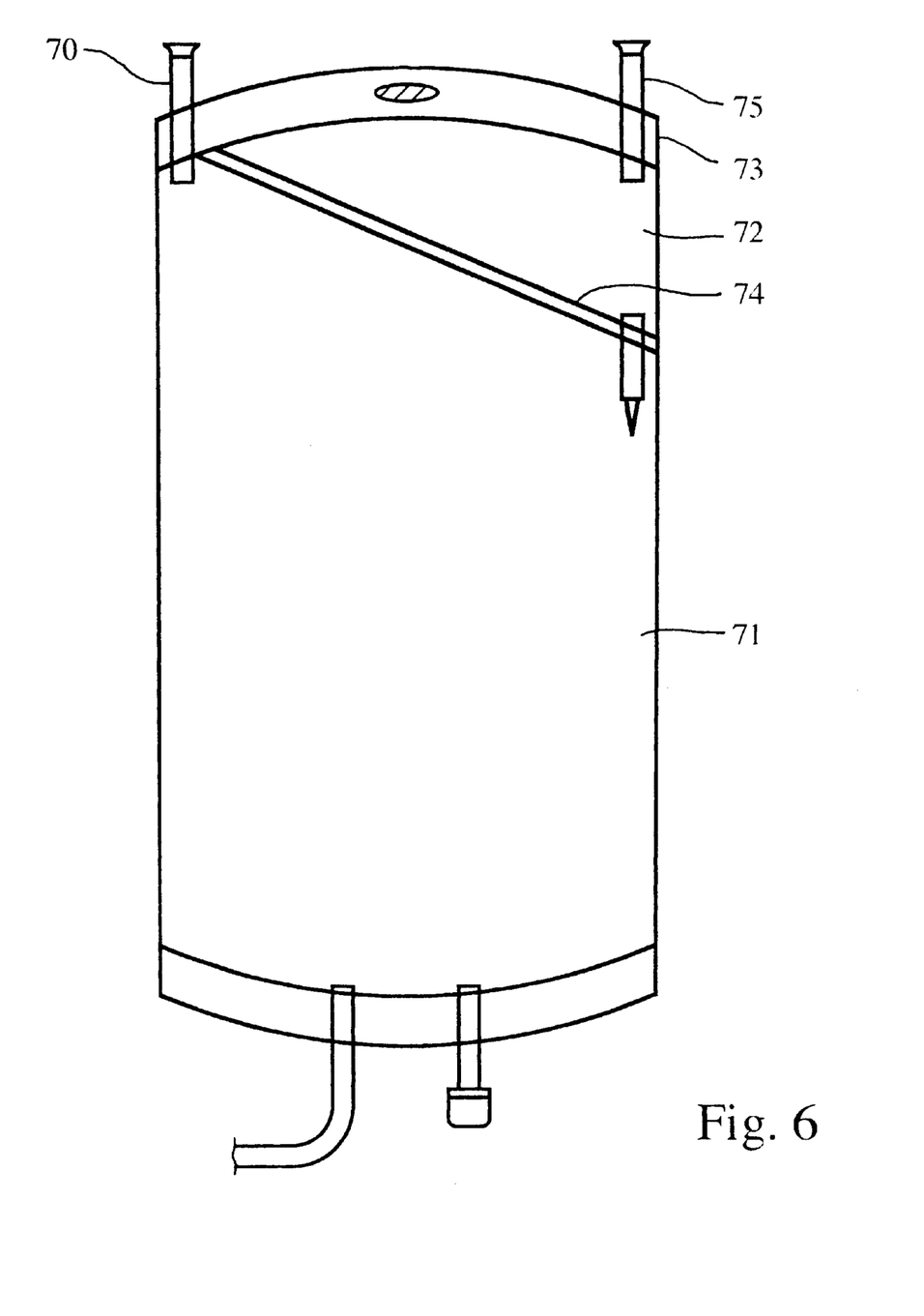
FIG. 6 is a plan view of a still further embodiment of the bag according to the invention.

FIG. 6 shows another embodiment of the invention which is rather similar to the embodiment shown in FIG. 2 but including an introduction tube to the large compartment 71 from the upper border 73. The division line between the upper compartment 72 and the lower compartment 71 is an inclined welding line 74 forming a triangular or substantially triangular first compartment 72. At the apex of the triangular compartment 72, the first compartment 71 is available via border 73 and the introduction tube 70 is inserted in that place. It is realized that if the inclined welding line 74 is more similar to welding line 24 shown in FIG. 2, the introduction tube 70 can have a sufficient length for passing through border 73, first compartment 72 and into the second compartment 71 via the welding line 74 (not shown in FIG. 6).

Figure 7:
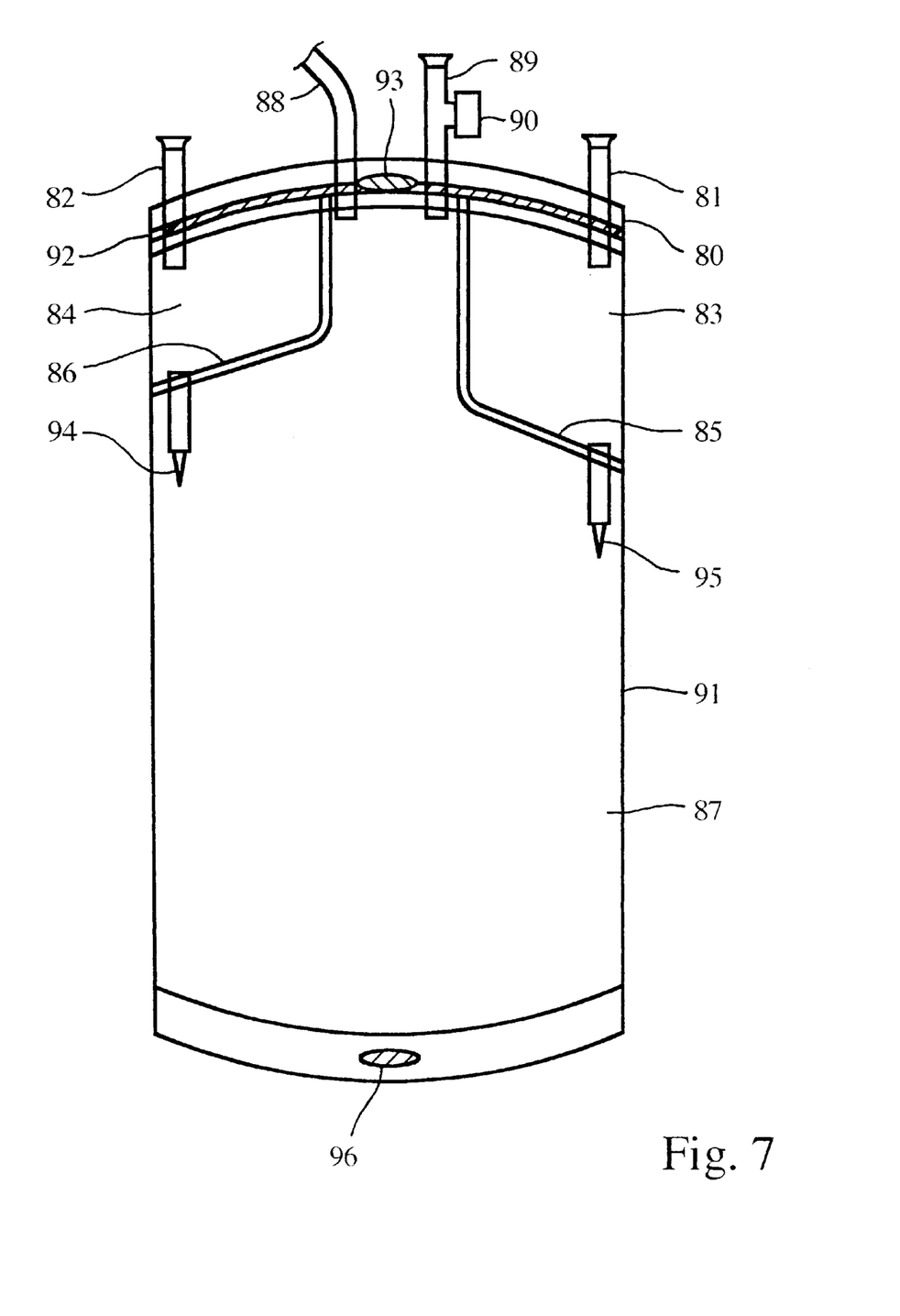
FIG. 7 is a plan view of another embodiment of the bag according to the invention.

It is realized that the different features shown on the different embodiments can be combined in different manners to obtain desired benefits and requirements. Further embodiments are possible, such as including all tubes in a single border. Such an embodiment is shown in FIG. 7. The upper border 80 comprises two introduction tubes ending in first compartment 83 and second compartment 84 for introduction of a glucose solution of a high concentration therein. Compartments 83 and 84 are delimited by welding lines 85,86 leaving the central portion of border 80 open towards the large bottom compartment 87. In the central portion of border 80 is placed an outlet tube 88 and a combined introduction tube 89 and medicament introduction port 90.

Since all connections are included in border portion 80, it can be made as a single separate injection moulded part, to which the bag blank 91 is welded as shown by welding lines 92.

When using the bag according to FIG. 7, it is supported in the position shown in FIG. 7 via aperture 93 and the respective breakable portions 94,95 are broken to mix the contents of compartment 83 and/or 84 with the contents of compartment 87. When the mixing procedure is ended, the bag is reversed and supported from the other direction from the aperture 96, whereupon outlet tube 88 will be positioned in the lowermost part of the bag. In this way, the mixing of the different solutions will be further improved.

Such a moulded part can have sealing surfaces to the manufacturing and filling equipment which makes it more convenient to the filling procedure. The moulded part can include grip portions for easy handling during storage and use etc.

Figure 8:
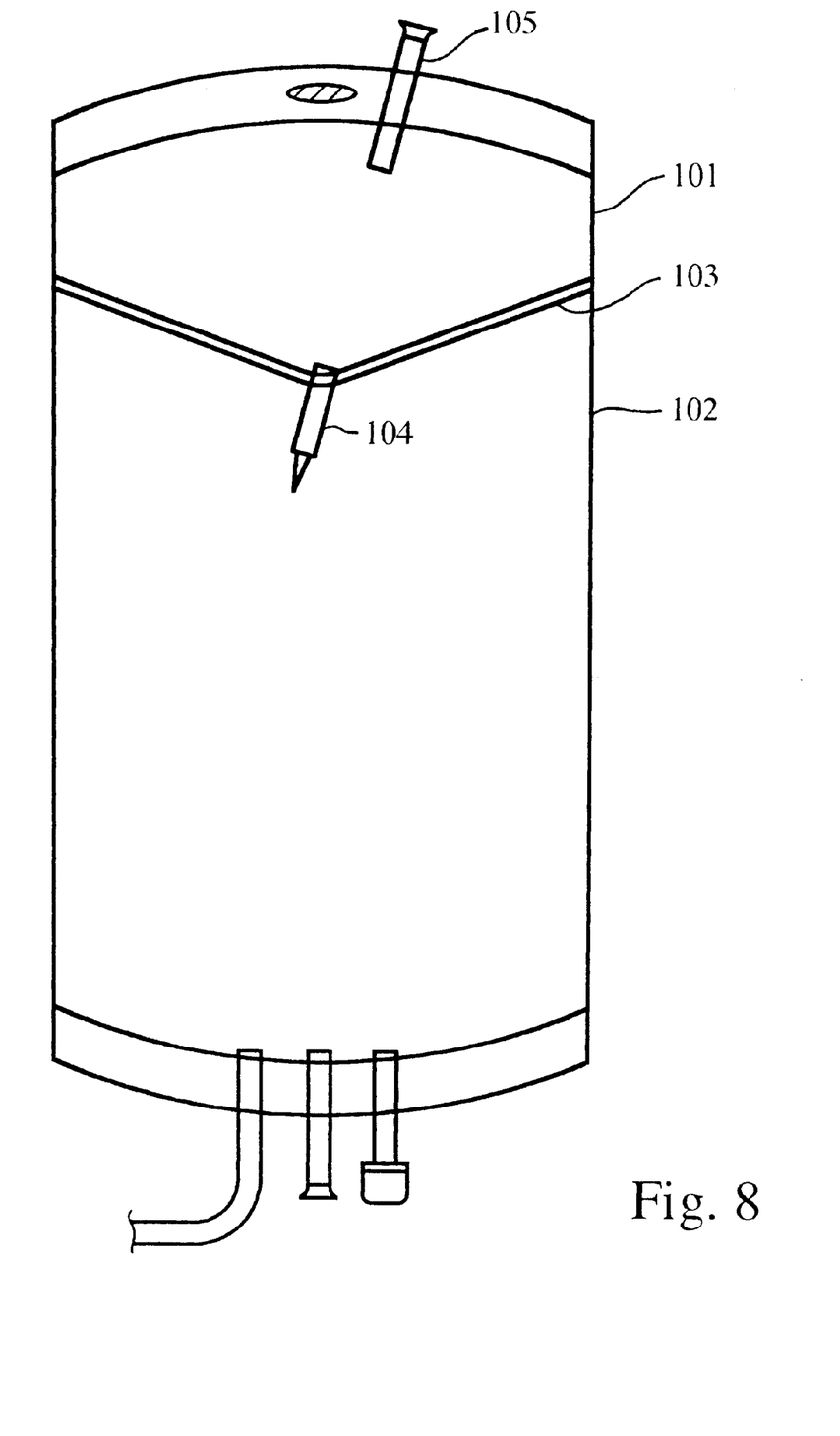
FIG. 8 is a plan view of yet another embodiment of the bag according to the invention.

Another embodiment of the invention is shown in FIG. 8. This embodiment includes two compartments 101,102 separated by a welding line 103 having a V-shape. In the appex. of the V-shape the connection tube 104 is inserted having a breakable portion. In the upper border of the bag, an introduction tube 105 is inserted. In other respects it is similar to the embodiment according to FIG. 2.

Figure 9:
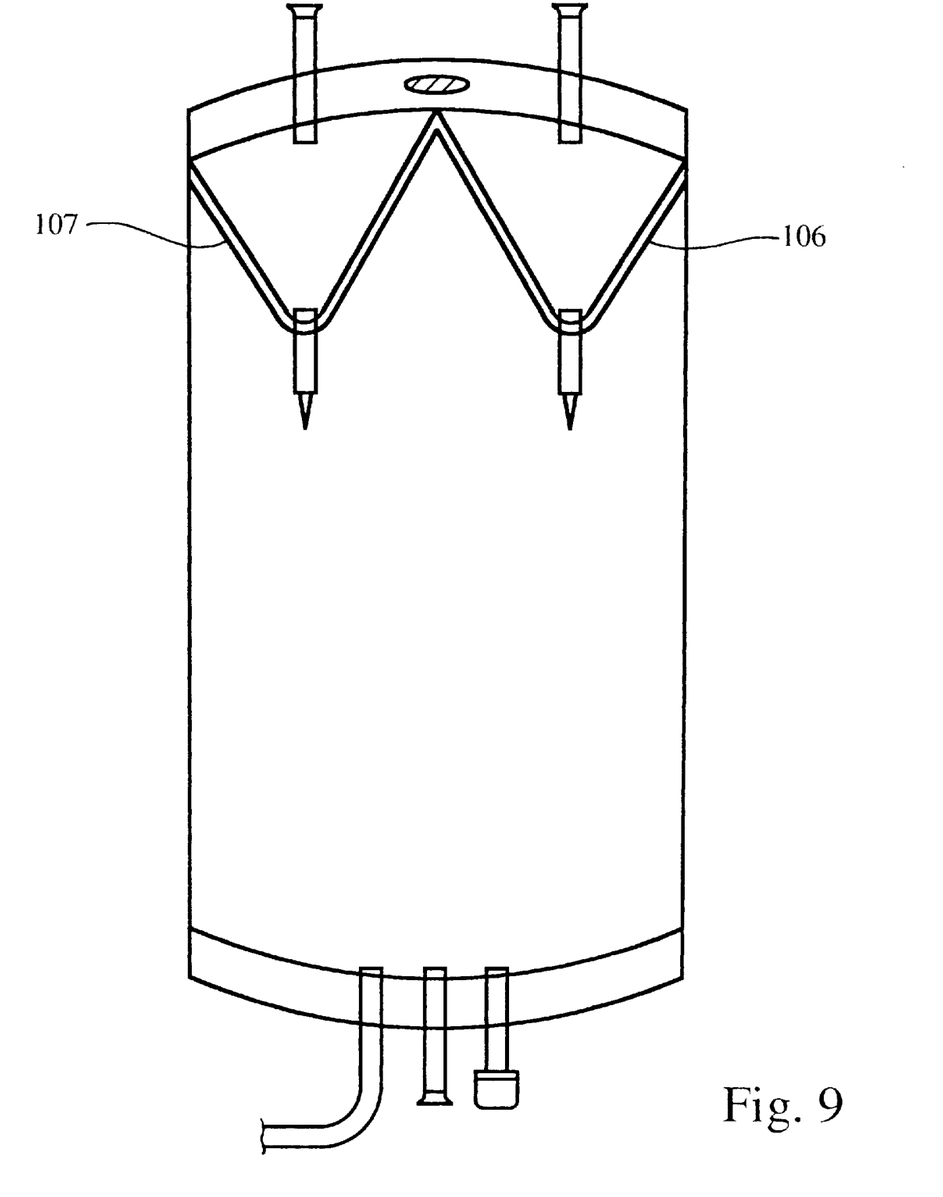
FIG. 9 is a plan view of another embodiment of the bag according to the invention.

Another variant of the present invention is shown in FIG. 9. The bag according to FIG. 9 comprises three compartments formed by two V-shaped welding lines 106,107. In other respects this embodiment is similar to the embodiment shown in FIG. 4.

Figure 10:
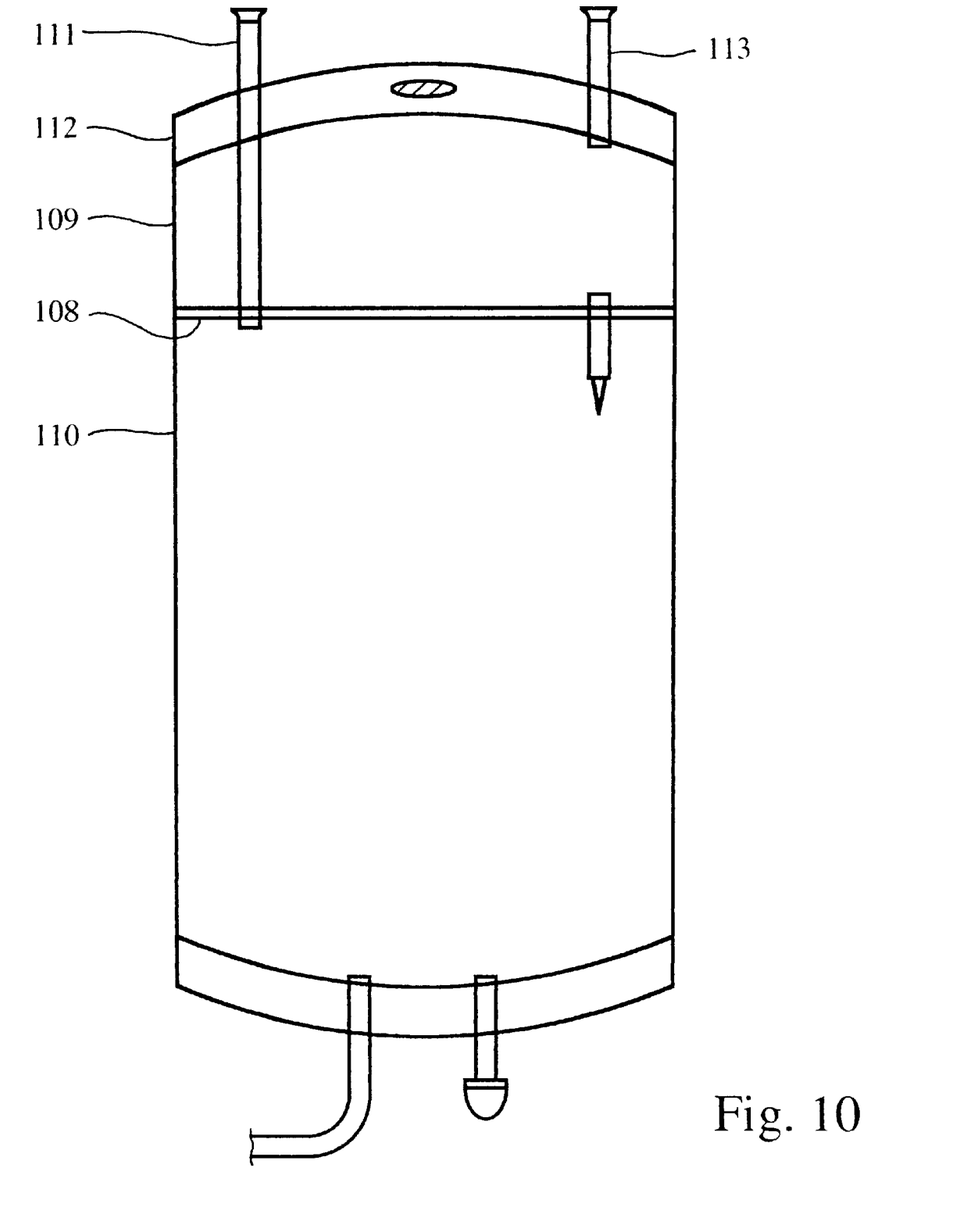
FIG. 10 is a plan view of yet another embodiment of the bag according to the invention.

FIG. 10 shows a variant of the embodiment shown in FIG. 6, where the sealing line 108 between the two compartments 109,110 is essentially horizontal. An introduction tube 111 for the electrolyte solution intended for compartment 110 extends through the upper border edge and through compartment 109 and line 108 into compartment 110. A second introduction tube 113 is connected to compartment 109. In other respects this embodiment is similar to the embodiment according to FIG. 6.

Figure 11:
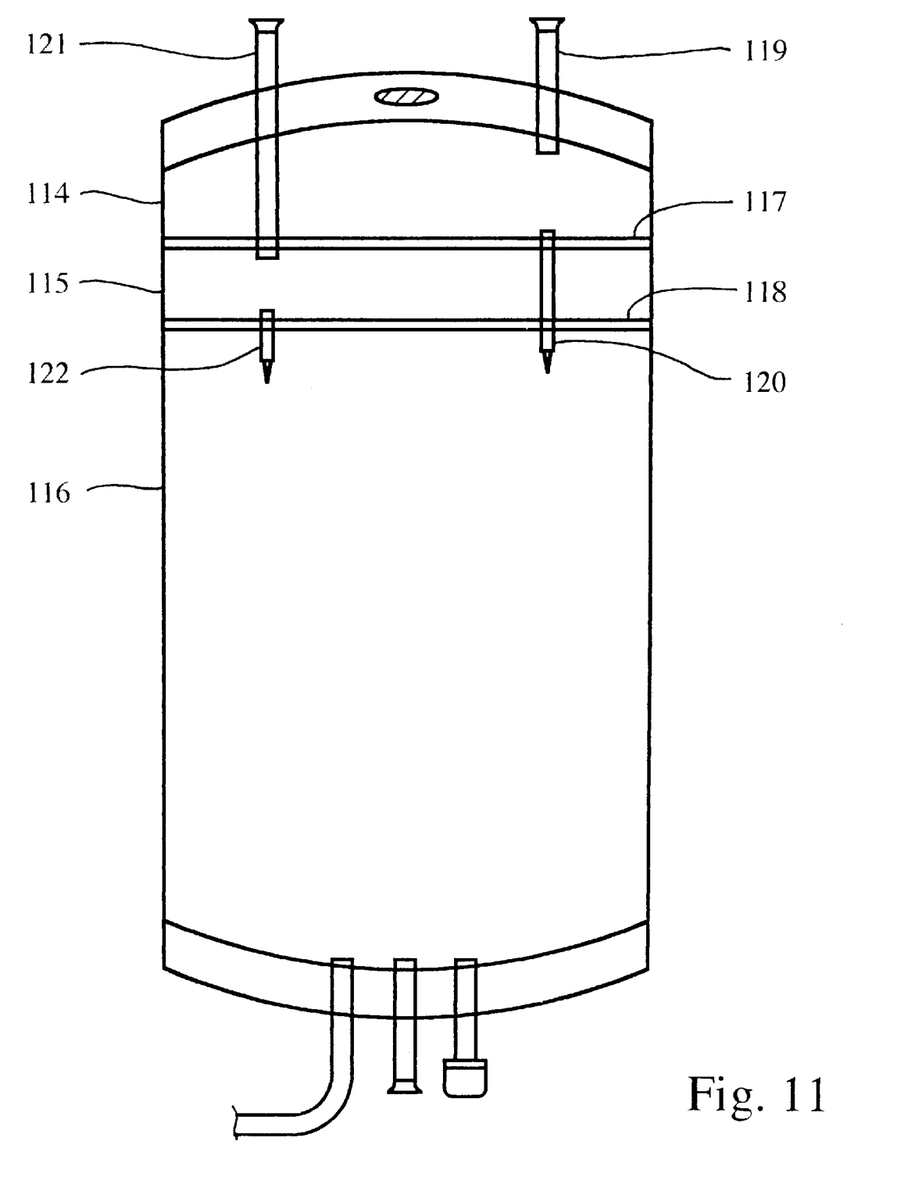
FIG. 11 is a plan view of a further embodiment of the bag according to the invention.

FIG. 11 shows a variant of the embodiment according to FIG. 4 and includes three compartments 114,115 and 116 formed by welding lines 117 and 118. The upper compartment 114 is filled with glucose solution via introduction tube 119 and is connected to the large bottom compartment 116 via a connection tube 120 extending from the upper compartment 14 beyond the intermediate compartment 115 to the lower compartment 116. The second compartment 115 is filled with glucose solution via introduction tube 121 extending from the upper border edge through compartment 114 to compartment 115. Compartment 115 is connected to compartment 116 via connection tube 122. In all other respects this embodiment is similar to the embodiment according to FIG. 4.

Figure 12:
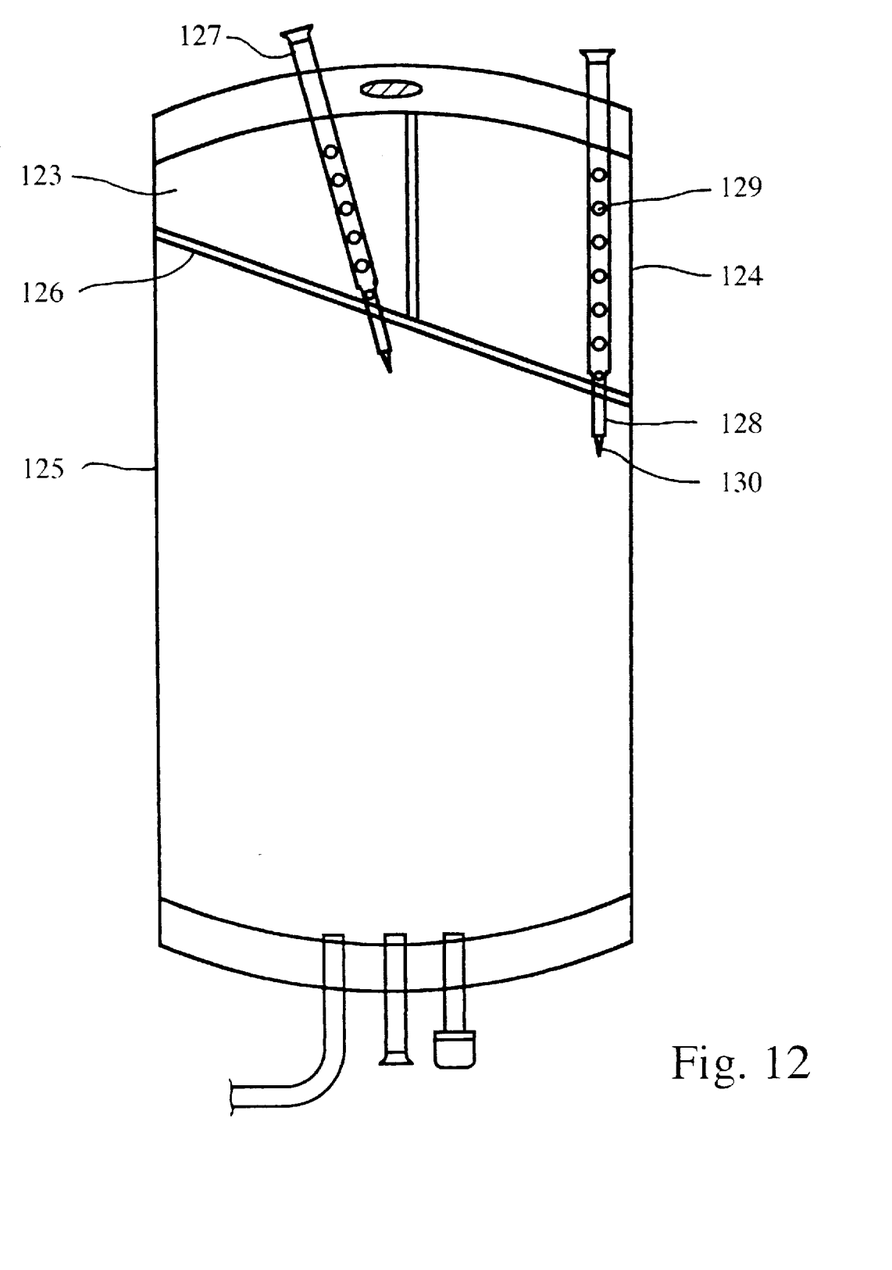
FIG. 12 is a plan view of another embodiment of the bag according to the invention.

Finally, FIG. 12 shows another embodiment of the invention having three compartments 123,124 and 125. A welding line 126 limits the large compartment 125 comprising electrolyte solution from compartments 123 and 124 comprising glucose solution. Welding line 126 is inclined and comprises two connection tubes 127,128. The operation is similar to the embodiment according to FIG. 4.

Each connection tube 127, 128 is provided with several holes 129 connecting tube 127, 128 to the compartment 123, 124 for glucose, and a break pin 130 connecting tube 127,128 with the large compartment 125. In this way the connection tube operates both as an introduction tube similar to tubes 46,47 of FIG. 4 and as a connection tube similar to tubes 48, 49 of FIG. 4. Thus, a smaller number of tubes are required.

Several different embodiments of the invention has been described above with reference to FIG. 2–12. The different detailed constructions of each embodiment can be combined in further different ways.

It is realized that the bag will have different sizes depending on the intended field of use. The concentration and other features of the glucose-part can be different depending on the actual use, such as 20%–50% or even more.

Herein above, several embodiments of the invention has been described in the purpose of exemplifying the invention. The invention is only limited by the appended patent claims.

We claim:

1. A container for sterile medical solutions including glucose, said container comprising a front side, a back side, a top border and a bottom border, separation means joining said front and back sides of said container so as to create at least first, second and third compartments within said container, said first compartment hang a sufficient size to accommodate said sterile medical solution including glucose and including an electrolyte solution, said second and third compartments including high concentration glucose solutions, a first openable connector for selectively connecting said first and second compartments upon opening said first openable connector in order to mix said glucose solution in said second compartment with said electrolyte solution in said first compartment, and a second openable connector for selectively connecting said first and third compartments upon opening said second openable connector in order to mix said glucose solution in said third compartment with said electrolyte in said first compartment, whereby a sterile medical solution including glucose can be produced in said first compartment with the least three different selected concentrations of said glucose therein.

2. The container of claim 1 wherein said second and third compartments have substantially the same volume.

3. The container of claim 1 wherein said second compartment has a greater volume than said third compartment.

4. The container of claim 3 wherein said high concentration glucose solutions in said second and third compartments are substantially the same.

5. The container of claim 1 wherein said high concentration glucose solution in said second compartment comprises approximately 60 ml of 50% glucose solution, said high concentration glucose solution in said third compartment comprises approximately 100 ml of 50% glucose solution, and said electrolyte comprises about 1900 ml including about 262 mMoles of $Na^+$, about 190 mMoles of $Cl^-$, about 2.7 mMoles of $Ca^{++}$, about 0.5 mMoles $Mg^{++}$ and about 80 mMoles of lactate.

6. The container of claim 1 wherein said separation means includes inclined portions corresponding to said second and third compartments, said inclined portions being inclined with respect to the horizontal when said container is supported from said top border in a first position.

7. The container of claim 6 including a first introduction tube disposed in said top border for introducing a fluid into said second compartment and a second introduction tube disposed in said top border for introducing a fluid into said third compartment.

8. The container of claim 7 wherein said top border comprises a separate member from said container, and wherein said front and back sides of said container are sealingly attached to said top border.

9. The container of claim 7 including a third introduction tube disposed in said top border for introducing a fluid into said first compartment.

10. The container of claim 1 wherein said first and second openable connectors comprise first and second tubular members and first and second breakable portions.

11. A method for mixing a sterile medical solution having at least three selectable glucose concentrations comprising providing a container including a first compartment accommodating said sterile medical solution and containing an electrolyte solution, a second compartment containing a high concentration glucose solution, and a third compartment containing a high concentration glucose solution, and providing fluid communication between said first compartment and at least one of said second and third compartments for mixing the contents thereof in order to provide a sterile medical solution having a selected concentration of glucose.

12. The method of claim 11 including providing fluid communication between said first, second and third compartments to provide a sterile medical solution having a predetermined concentration of glucose.

* * * * *

UNITED STATES PATENT AND TRADEMARK OFFICE
CERTIFICATE OF CORRECTION

PATENT NO. : 6,039,719
DATED : March 21, 2000
INVENTOR(S) : Wieslander et al.

It is certified that error appears in the above-identified patent and that said Letters Patent is hereby corrected as shown below:

Title Page,
Item [75], "Genoa" should read --Genova--.
Item [56], "Littenburg" should read --Littenberg--.

Column 2,
Line 7, further embodiment" should read --further embodiments--.

Column 3,
Line 57, "risk of 25 leakages" should read --risk of leakages--.

Column 4,
Line 29, "45 is mixed" should read --45 are mixed--.
Line 55, "very much ressembles" should read --very much resembles--.
Line 60, "ties appears" should read --ties appear--.

Column 6,
Line 34, "partment 14" should read --partment 114--.
Line 57, "invention has" should read --invention have--.

UNITED STATES PATENT AND TRADEMARK OFFICE
CERTIFICATE OF CORRECTION

PATENT NO. : 6,039,719
DATED : March 21, 2000
INVENTOR(S) : Wieslander et al.

It is certified that error appears in the above-identified patent and that said Letters Patent is hereby corrected as shown below:

Column 6,
Line 58, "to FIG. 2-12" should read --to FIGS.2-12--
Line 65, "invention has" should read --invention have--.

Column 7,
Line 21, "the least" should read --the at least--.

Signed and Sealed this

Third Day of July, 2001

*Attest:*

*Attesting Officer*

NICHOLAS P. GODICI
*Acting Director of the United States Patent and Trademark Office*